United States Patent [19]
Möller et al.

[11] Patent Number: 5,651,041
[45] Date of Patent: Jul. 22, 1997

[54] APPARATUS FOR MEASURING THE DENSITY OF ACCUMULATIONS OF FIBROUS MATERIAL IN ROD MAKING MACHINES OF THE TOBACCO PROCESSING INDUSTRY

[75] Inventors: Henning Möller, Hamburg; Reinhard Hoppe, Tespe, both of Germany

[73] Assignee: Hauni Maschinenbau AG, Hamburg, Germany

[21] Appl. No.: 635,436

[22] Filed: Apr. 18, 1996

[30] Foreign Application Priority Data

May 20, 1995 [DE] Germany ............. 195 18 640.0

[51] Int. Cl.$^6$ ............................................. G01B 15/02
[52] U.S. Cl. ................................... 378/54; 131/905
[58] Field of Search ........................... 131/280, 84.1, 131/905; 378/54

[56] References Cited

U.S. PATENT DOCUMENTS

| | | | |
|---|---|---|---|
| 3,056,026 | 9/1962 | Bigelow. | |
| 4,424,443 | 1/1984 | Reuland | 250/252.1 |
| 4,616,139 | 10/1986 | Heitmann | 131/905 |
| 4,805,641 | 2/1989 | Radzio et al. | 131/280 |
| 4,865,054 | 9/1989 | Lorenzen et al. | 131/905 |
| 4,889,138 | 12/1989 | Heitmann et al. | 131/84.1 |
| 5,009,238 | 4/1991 | Heitman | 131/108 |
| 5,072,741 | 12/1991 | Heitmann | 131/84.1 |

*Primary Examiner*—Don Wong
*Attorney, Agent, or Firm*—Darby & Darby

[57] ABSTRACT

The density of successive increments of two neighboring rod-like flows of tobacco particles in a cigarette rod making machine is determined by an apparatus which employs a source serving to emit a divergent beam of X-rays across the paths for the two flows so that the radiation which has penetrated through and issues from the two flows is indicative of the density of the respective flows. Such intensity is ascertained by discrete X-ray detectors which transmit corresponding signals to an evaluating circuit. The latter compares such signals with a reference signal denoting the intensity of a portion of radiation which has bypassed the flows, and the evaluating circuit can further compensate for the difference, if any, between the distances of the two paths from the radiation source.

13 Claims, 1 Drawing Sheet

U.S. Patent
Jul. 22, 1997
5,651,041
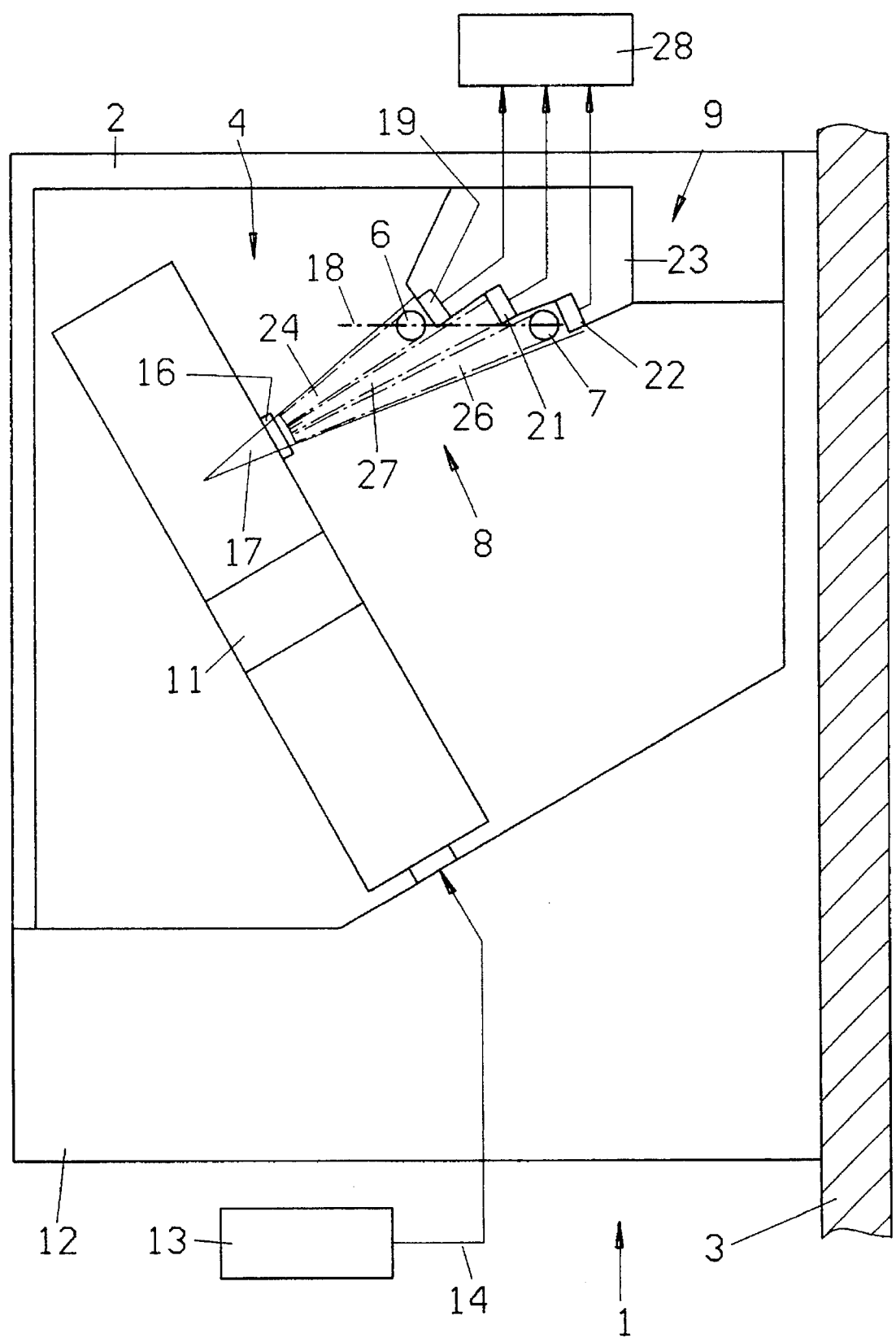

APPARATUS FOR MEASURING THE DENSITY OF ACCUMULATIONS OF FIBROUS MATERIAL IN ROD MAKING MACHINES OF THE TOBACCO PROCESSING INDUSTRY

BACKGROUND OF THE INVENTION

The invention relates to improvements in density measuring apparatus and methods in general, and more particularly to improvements in apparatus for and in methods of measuring or ascertaining the density of successive increments of running flows (such as streams, rods, fillers or the like) of particulate fibrous material. Still more particularly, the invention relates to improvements in methods of and in apparatus for ascertaining the density of flows of accumulations of fibrous material of the type being manipulated in various types of machines which are utilized in the tobacco processing industry. Typical examples of such machines are those for the making of continuous rods which are ready to be subdivided into plain cigarettes, cigars, cigarillos or cheroots of unit length or multiple unit length.

It is already known to construct and assemble a cigarette rod making machine (also known as maker) in such a way that it can turn out a plurality of (particularly two) continuous cigarette rods wherein a rod-shaped filler of natural, artificial and/or reconstituted tobacco is draped into a continuous wrapper of cigarette paper or the like and is subdivided into plain cigarettes of unit length or multiple unit length. As a rule, successive increments of each filler of particulate fibrous material are being monitored in order to ascertain their density, i.e., a characteristic which is important to maintain the quality of the cigarettes within an acceptable range. Uniform density or a density which is maintained within a predetermined range is important to ensure that the quantity of tobacco from cigarette to cigarette, as well as within a discrete cigarette, does not fluctuate at all or fluctuates only within an acceptable range. Such uniform or practically uniform density can be achieved by ensuring that each of a short or long series of successively produced cigarettes (or cigars, cigarillos or cheroots) contains a predetermined quantity of particles as well as that the particles are uniformly distributed from end to end. The so-called filling power of rod-shaped smokers' products can be ascertained by determining, with a requisite degree of accuracy, the density of the rod-shaped fillers of such products.

As a rule, the density of fillers in cigarettes or analogous rod-shaped products of the tobacco processing industry (hereinafter referred to as cigarettes for short) is determined by resorting to a source of radioactive radiation, such as a strontium 90 preparation which emits beta rays. Reference may be had, for example, to U.S. Pat. No. 4,424,443. The drop in the intensity of radiation which has penetrated through a flow of tobacco particles is indicative of the density of successive increments of such flow. An advantage of a density measuring apparatus which employs a source of beta rays is that the results (namely the density measurements) are highly reliable. However, such apparatus also exhibit certain serous drawbacks, particularly as concerns their cost, because their installation in or their utilization in conjunction with cigarette rod making machines renders it necessary to carry out extensive, costly, complex and bulk-increasing undertakings to ensure the safety of attendants in a cigarette making plant.

It is also known to ascertain the density of a continuous flow of tobacco or analogous particulate material for use in the tobacco processing industry by employing a density measuring apparatus which is equipped with a source of infrared radiation. Reference may be had, for example, to U.S. Pat. No. 4,805,641. An advantage of such apparatus is that the aforediscussed undertakings to ensure the safety of attendants can be simplified or omitted. However, the reliability of an apparatus which operates with infrared radiation is not as satisfactory as that of an apparatus which operates with beta rays.

In accordance with a further proposal (disclosed in U.S. Pat. No. 3,056,026), the apparatus for monitoring the density of a flow of tobacco particles or other particulate material of the tobacco processing industry can employ a source of X-rays. However, presently known apparatus of such character have also failed to satisfy all of the requirements concerning the safety of the attendants, low cost, compactness, versatility and accuracy of determination of the density of successive increments of a rapidly running flow in the form of a rod, filler or stream of particulate material.

Another drawback of all heretofore known density measuring apparatus of the above outlined character is that they are incapable of simultaneously monitoring the densities of several rapidly advancing flows of particulate material which includes or consists of natural, artificial and/or reconstituted tobacco. On the other hand, many presently known cigarette makers are designed to simultaneously produce several continuous cigarette rods which can be subdivided into discrete files of plain cigarettes of unit length or multiple unit length. Reference may be had, merely by way of example, to U.S. Pat. Nos. 4,889,138, 5,009,238 and 5,072,741. Therefore, a machine which is designed to simultaneously turn out several continuous cigarette rods must be equipped or combined with a discrete density measuring apparatus for the particulate material of each cigarette rod. This contributes to the bulk and cost of such machines and renders it likely that the quality of density measuring operation which is carried by one density measuring apparatus will depart from the quality of the density measuring operation carried out by the other apparatus.

The disclosures of all patents which are enumerated in the specification of the present application are incorporated herein by reference.

OBJECTS OF THE INVENTION

An object of the invention is to provide a novel and improved apparatus which is constructed and assembled in such a way that it can simultaneously ascertain the density of successive increments of several continuous flows of particulate material of the type being manipulated in various machines of the tobacco processing industry.

Another object of the invention is to provide a novel combination of parts which are being utilized in the improved apparatus.

A further object of the invention is to provide a novel and improved combination of a machine for simultaneous production of a plurality of continuous cigarette rods and apparatus for ascertaining the density of successive increments of such rods.

An additional object of the invention is to provide an apparatus which can be utilized with advantage for the above outlined purposes and whose space requirements are but a fraction of those of apparatus heretofore employed to ascertain the density of dual rods being turned out by a cigarette maker or another rod making machine of the tobacco processing industry.

Still other object of the invention is to provide a novel and improved combination of radiation emitting means and means for guiding plural flows of particulate material in the above outlined apparatus.

A further object of the invention is to provide an apparatus wherein the means for emitting radiation is less likely to represent a danger to the attendants than a source of nuclear radiation, such as beta rays.

Another object of the invention is to provide an apparatus which can be combined with or incorporated in existing models of machines for the production of single or plural continuous flows of particulate material of the type being manipulated in the tobacco processing industry.

An additional object of the invention is to provide an apparatus which, though not employing beta rays, is just as reliable and just as accurate as presently known apparatus which employ beta rays or other nuclear radiation.

Still other object of the invention is to provide an apparatus which can employ a single radiation source in spite of the fact that it is capable of simultaneously ascertaining the densities of plural flows of particulate material such as rod-like fillers of natural, artificial and/or reconstituted tobacco.

A further object of the invention is to provide an apparatus which can simultaneously ascertain the densities of plural rod-like tobacco fillers at a fraction of the cost involved in employing a discrete density measuring apparatus for each filler.

Another object of the invention is to provide a novel and improved method of simultaneously ascertaining the densities of two adjacent but spaced-apart running flows of particulate material of the type being manipulated in the tobacco processing industry.

An additional object of the invention is to provide a novel and improved method of simultaneously ascertaining the densities of successive increments of parallel rod-like fillers being turned out by a dual cigarette rod maker or an analogous machine.

SUMMARY OF THE INVENTION

The invention is embodied in an apparatus for simultaneously measuring the density of a plurality of flows (such as so-called fillers which constitute rod-like accumulations of tobacco particles) which contain particulate material for use in the tobacco processing industries and advance along predetermined paths. The improved apparatus comprises a source of X-rays which serves to emit radiation across each of the paths so that the intensity of radiation which has penetrated through and issues from the flows in the paths is indicative of the density of the respective flows, and signal generating means for individually ascertaining the intensity of radiation issuing from each of the flows.

The particulate material is or can include or constitute tobacco, and the flows can constitute substantially rod-like streams of tobacco particles. The paths can include a first path and a second path which is adjacent the first path. The signal generating means can include an X-ray detector for each of the first and second paths.

The source of X-rays can be positioned and oriented to emit radiation a portion of which bypasses the paths, and the signal generating means can include a discrete X-ray detector for radiation issuing from the flow in each of the paths, and an additional X-ray detector for ascertaining the intensity of the aforementioned portion of radiation (namely the radiation which has bypassed the flows in the plurality of paths) and for generating reference signals denoting the intensity of such portion of radiation.

It is presently preferred to employ a source which includes means for emitting a beam of radiation which diverges from the source at an angle of at least 20°.

The paths can include first and second paths which are disposed in a predetermined plane (e.g., a horizontal plane) and have portions extending through a testing station or zone, and the source of X-rays can include means for emitting across the testing station a beam of radiation at an oblique angle to the predetermined plane.

The signal generating means can include at least one silicon photodiode.

The apparatus can further comprise means for evaluating signals which are transmitted by the signal generating means. If the source of X-rays is positioned in such a way that it is located at a first distance from a first one of the plurality of paths and at a different second distance from a second one of the plurality of paths, the evaluating means preferably comprises means for influencing the signal or signals generated by the signal generating means for at least one of the first and second paths in order to compensate for the difference between the first and second distances.

The paths can include spaced-apart first and second paths, and the source of X-rays can be arranged to emit a beam of radiation across and between the first and second paths. The signal generating means of such apparatus can include first and second detectors for radiations issuing from the flows in the first and second paths, respectively, and a third detector for radiation propagating itself between the first and second paths.

The signal generating means can include a battery of X-ray detectors and a common support for the battery. For example, the battery can include or constitute a row of detectors.

The source and the signal generating means (and, if desired, also the signal evaluating means) can form part of a module which is designed to be preferably removably installed in a rod making machine of the tobacco processing industry. For example, such machine can constitute a dual cigarette rod making machine.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain presently preferred specific embodiments with reference to the accompanying drawings.

BRIEF DESCRIPTION OF THE DRAWING

The single FIGURE of the drawing is a diagrammatic view of an apparatus which is designed to be used in a machine for the simultaneous production of two cigarette rods.

DESCRIPTION OF PREFERRED EMBODIMENTS

The single FIGURE of the drawing illustrates a module 1 forming part of or constituting a density measuring apparatus for use in or in combination with a dual cigarette rod making machine of the type disclosed, for example, in the aforementioned U.S. Pat. Nos. 4,889,138 or 5,009,238 or 5,072,741 (all owned by the assignee of the present application). The module 1 includes an enclosure or housing 2 which is preferably separably affixed (in a manner not specifically shown in the drawing) to a frame 3 of the dual cigarette rod maker (e.g., a maker in a filter cigarette production line known as PROTOS 2 and produced and distributed by the assignee of the present application). As already mentioned above, the housing 2 of the module 1 is preferably detachable from the frame 3 in order to facilitate and simplify its inspection, cleaning and/or repair. Moreover, the module 1 can be installed in or combined with existing makers of plural rods which contain fragments of tobacco and/or other particulate material of the type being manipulated in the tobacco processing industry.

The apparatus including the module 1 comprises a source 4 which is designed to discharge a divergent beam 8 of radiation, namely X-rays, and signal generating means 9 which includes a discrete detector (shown at 19 and 22) for radiation that has penetrated through and is issuing from the respective flows 6 and 7 of particulate material. The flows are advanced along two discrete parallel paths which extend at right angles to the plane of the drawing and include portions or sections extending through a testing zone or testing station where they are raversed by the beam 8 of radiation issuing from the X-ray source 4. The intensity of radiation which has penetrated through and issues from successive increments of the flows 6 and 7 is indicative of the density of the monitored increments, and such intensity is ascertained by the respective detectors 19, 22 which transmit appropriate signals to the corresponding inputs of a signal evaluating circuit 28.

The illustrated radiation source 4 includes an emitter 11 of X-rays (e.g., a tube) which is installed in or on a holder (e.g., a pedestal) 12 carried by or forming part of the housing 2o The reference character 14 denotes a conductor which connects the source 4 with a source 13 of high potential necessary to enable the emitter 11 to furnish a beam 8 possessing the required characteristics. The source 4 is further provided with customary additional connections which are necessary to render the emitter 11 operative (such additional connections are or can be provided in the holder 12 and are not specifically shown in the drawing).

The beam 8 of X-rays issues from the source 4 through a window 16 and diverges at an angle 17 of preferably not less than 20 degrees.

The paths for the two illustrated flows 6 and 7 are located in a common plane 18 and are spaced apart from each other so that a portion 27 of the beam 8 can advance between the two paths without penetrating into a flow of particulate material. Such portion 27 of the beam 8 is flanked by portions 24 and 26 which respectively traverse the paths for the flows 6 and 7 at different distances from the window 16 of the source 4.

As mentioned above, the intensity of radiation (beam portion 24) issuing from successive increments of the flow 6 is ascertained by a first detector 19 which transmits appropriate signals to the corresponding input of the evaluating circuit 28, and the intensity of radiation (beam portion 26) issuing from successive increments of the flow 7 is ascertained by a second detector 22 which transmits appropriate signals to the corresponding input of the circuit 28. A third detector 21 ascertains the intensity of the portion 27 of the beam 8 and transmits corresponding (reference) signals to a further input of the circuit 28. The three detectors 19, 21 and 22 together form a battery in the form of a row mounted on a common support 23, and those sides or surfaces of the detectors 19, 21 and 22 which face the respective portions 24, 27, 26 of the beam 8 are suitably inclined relative to the plane 18.

The drawing shows that the orientation of the source 4 relative to the paths for the flows 6 and 7 is such that the beam 8 of X-rays makes with the plane 18 an oblique angle. This contributes to the compactness of the density measuring apparatus because it is possible to place the window 16 close to the paths for the flows 6 and 7. Furthermore, a single beam 8 suffices to penetrate across successive increments of the two flows 6 and 7 in spite of the shortness of the distance between the window 16 and the plane 18 of the paths for the flows 6 and 7.

Another advantage of the aforediscussed closeness of the window 16 to the paths for the flows 6 and 7 is that the intensity of those portions (24 and 26) of the beam 8 which reach and penetrate through the respective flows of particulate material is still relatively high which contributes to accuracy of the determination of density, i.e., to the reliability of signals which the detectors 19 and 22 transmit to the corresponding inputs of the evaluating circuit 28 and which are to denote the density of the corresponding increments of the respective flows 6 and 7. An advantage of the illustrated position of the third detector 21 between the detectors 19 and 22 is that the entire width of the beam 8 can be utilized for the determination of intensity of the respective portions of the beam 8 for the generation of signals denoting the densities of the flows 6, 7 and for the generation of a reference signal.

The reference signals furnished by the detector 21 are utilized to ascertain whether or not the intensity of radiation (beam 8) issuing through the window 16 is constant because eventual fluctuations of such intensity could affect the accuracy of signals which are transmitted by the detectors 19 and 22. In other words, in the absence of any compensation for fluctuations of the intensity of radiation issuing from the source 4, the signals transmitted by the detectors 19 and 22 could be interpreted as denoting non-existent fluctuations and/or other changes in the density of the respective increments of the flows 6 and 7. The evaluating circuit 28 comprises means for correcting the signals furnished by the detectors 19 and 22 in dependency upon fluctuations (if any) of the reference signals transmitted by the detector 21. Alternatively, or in addition, the evaluating circuit 28 can be utilized to alter the intensity of radiation issuing from the source 4 if such alteration is warranted on the basis of the characteristics of reference signals furnished by the detector 21.

The circuit 28 processes the signals from the detectors 19 and 22 into signals which are indicative of actual density of the monitored increments of the respective flows 6 and 7, and such processed signals are utilized to adjust (when necessary) those aggregates or units of the rod making machine which influence the density of the flows 6 and 7. This ensures that the density of the flows 6 and 7 is automatically adjusted if the monitored density departs from the desired or optimum density. As can be seen in the drawing, the window 16 is disposed at a first distance from the path for the flow 6 and at a greater second distance from the path for the flow 7. Therefore, the evaluating circuit 28 is constructed and assembled in such a way that it can compensate for the difference between the two distances, and more particularly for the influence of such difference upon the characteristics of signals which are being transmitted by the detectors 19 and 21. This can be achieved, for example, by relying on certain empirically determined data which are considered in the processing of signals received from the detector 19 and/or 21.

A presently preferred source of X-rays is a metal-ceramic X-ray tube known as Type MCB 40-1C which is distributed by the Firm rtw Röntgen-Technik Dr. Warrikhoff KG, D-15366 Neuenhagen, Federal Republic Germany. The detectors 19, 21 and 22 can be of any well known and readily available type of X-ray sensors; however, it is presently preferred to employ silicon photodiodes, for example, those known as Type CXM PSD distributed by the Firm Crystal, Berlin, Federal Republic Germany. It has been found that such detectors are capable of furnishing signals which are very accurately indicative of the intensity of measured or monitored X-rays.

An important advantage of the improved apparatus is its compactness so that it can be readily installed in existing rod making machines serving to turn out plural cigarette rods or analogous commodities of the tobacco processing industry. Furthermore, the improved apparatus is simpler, safer and less expensive than, but at least as reliable and accurate as, presently known apparatus which operate with sources of beta rays or other nuclear radiation.

Though the utilization of a source of X-rays also necessitates resort to some safety undertakings involving shielding and certain others, the cost and space requirements of such undertakings are merely a fraction of those which must be resorted to when a rod making machine employs one or more sources of beta rays. Furthermore, whereas a source of beta rays must be operated without interruptions, a source of X-rays can be turned on or off as often as necessary. Still further, when set up in a manner as described hereinbefore (or in an analogous manner), a single source of X-rays suffices to furnish radiation for simultaneous determination of the density of successive increments of plural flows in the form of streams, rods or fillers of particulate material, and this contributes significantly to savings in space and lower cost of the improved apparatus.

The positioning of the detector 21 for the transmission of reference signals between the detectors 19 and 22 also contributes to the simplicity, compactness, reliability and lower cost of the improved apparatus in comparison with plural testing apparatus which are presently in use in conjunction with machines for the making of plural cigarette rods or the like.

Since the module 1 can be readily installed in and removed from a rod making machine, it can be conveniently serviced outside of such machine. Moreover, the module 1 can be installed in existing machines as a superior substitute for plural density measuring apparatus, namely one for each rod of a maker of plural cigarette rods or the like.

All in all, the novel concept of utilizing a single radiation source in conjunction with plural detectors which monitor the intensities of portions of radiation issuing from a plurality of discrete flows of particulate material contributes to compactness and lower cost of the apparatus but without affecting the accuracy of intensity and density measurements.

As already mentioned above, the improved apparatus can employ any suitable available X-ray detectors. The aforementioned detectors known as Type CXM PSD are presently preferred because they have been found to be particularly sensitive within the energy range which is desirable in the improved apparatus as well as because they are of robust construction and relatively inexpensive.

The provision of a single common holder, carrier or support 23 for the battery of detectors 19, 21 and 22 constitutes an optional but desirable and advantageous feature of the improved module 1. The evaluating circuit 28 (the exact construction of which forms no part of the present invention) can also be mounted on or in the housing 2, i.e., such circuit can also form part of the module 1.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of the above outlined contribution to the art of density measurement and, therefore, such adaptations should and are intended to be comprehended within the meaning and range of equivalence of the appended claims.

What is claimed is:

1. Apparatus for simultaneously measuring the density of a plurality of flows which contain particulate material for use in the tobacco processing industry and advance along predetermined paths, comprising a source of X-rays arranged to emit radiation across each of said paths so that the intensity of radiation which has penetrated through and issues from the flows in said paths is indicative of the density of the respective flows; and signal generating means for individually ascertaining the intensity of radiation issuing from each of the flows.

2. The apparatus of claim 1, wherein the particulate material includes tobacco and said flows are substantially rod-like streams of particulate material, said paths including a first path and a second path adjacent said first path.

3. The apparatus of claim 2, wherein said signal generating means includes an X-ray detector for at least one of said paths.

4. The apparatus of claim 1, wherein said source is positioned to emit radiation a portion of which bypasses said paths and said signal generating means includes a discrete X-ray detector for radiation issuing from each of the flows and an additional X-ray detector for ascertaining the intensity of said portion of radiation and for generating reference signals denoting the intensity of said portion of radiation.

5. The apparatus of claim 1, wherein said source includes means for emitting a beam of radiation which diverges from the source at an angle of at least 20 degrees.

6. The apparatus of claim 1, wherein said paths include first and second paths disposed in a predetermined plane and having portions extending through a testing station, said source including means for emitting across said testing station a beam of radiation at an oblique angle to said predetermined plane.

7. The apparatus of claim 1, wherein said signal generating means includes at least one silicon photodiode.

8. The apparatus of claim 1, further comprising means for evaluating signals generated by said signal generating means, said source being disposed at a first distance from a first one of said paths and at a different second distance from a second one of said paths, said evaluating means comprising means for influencing the signal generated by the signal generating means for the flow in at least one of said first and second paths to compensate for the difference between said first and second distances.

9. The apparatus of claim 1, wherein said paths include spaced apart first and second paths and said source is arranged to emit a beam of radiation across and between the flows in said first and second paths, said signal generating means including first and second detectors for radiation issuing from the flows in said first and second paths, respectively, and a third detector for radiation propagating itself between said first and second paths.

10. The apparatus of claim 1, wherein said signal generating means includes a battery of X-ray detectors and a common support for said detectors.

11. The apparatus of claim 10, wherein said detectors of said battery include a row of detectors.

12. The apparatus of claim 1, wherein said source and said signal generating means form part of a module arranged to be removably installed in a rod making machine of the tobacco processing industry.

13. The apparatus of claim 12, wherein said machine is a dual cigarette rod making machine.

* * * * *